United States Patent [19]
Kuizenga et al.

[11] Patent Number: 5,178,617
[45] Date of Patent: Jan. 12, 1993

[54] SYSTEM FOR CONTROLLED DISTRIBUTION OF LASER DOSAGE

[75] Inventors: Dirk J. Kuizenga, Sunnyvale; Mark V. Ortiz, San Jose, both of Calif.

[73] Assignee: Laserscope, San Jose, Calif.

[21] Appl. No.: 727,560

[22] Filed: Jul. 9, 1991

[51] Int. Cl.⁵ .............................................. A61N 5/06
[52] U.S. Cl. ........................................ 606/17; 606/9; 606/11
[58] Field of Search .................. 606/2, 3, 7, 8, 9, 10, 606/11, 12, 13, 16, 17; 128/395-398

[56]         References Cited
U.S. PATENT DOCUMENTS

| 4,669,467 | 6/1987 | Willett et al. | 606/17 X |
| 4,860,172 | 8/1989 | Schlager et al. | 606/17 X |
| 4,911,711 | 3/1990 | Telfair et al. | 606/11 X |
| 5,000,752 | 3/1991 | Hoskin et al. | 606/17 X |
| 5,066,292 | 11/1991 | Müller et al. | 606/7 |

FOREIGN PATENT DOCUMENTS 8706478  5/1987  PCT Int'l Appl. .

OTHER PUBLICATIONS

Fiber Bundle Scanner for Laser Photocoagulation Treatment, Fujii et al, 1982 Butterworth & Co (Publishers) Ltd.

Primary Examiner—Peter A. Aschenbrenner
Attorney, Agent, or Firm—Fliesler, Dubb, Meyer & Lovejoy

[57]         ABSTRACT

A mechanism for distributing the output beam from a laser system in a treatment pattern that comprises a plurality of optical fibers, having input ends and output ends. At the input ends, the fibers are secured in a scan configuration for receiving an output beam from a laser. At the output ends, the fibers are configured in a treatment configuration for distributing the output beam in a treatment pattern. A scanner coupled with the laser system directs the beam in a scan pattern at the input ends of the fibers which matches the scan configuration. The treatment configuration secures the output ends of the optical fibers so that the output end of one optical fiber sequentially receiving the beam from the scanner is non-adjacent the output end of a next optical fiber sequentially receiving the beam from the scanner.

14 Claims, 3 Drawing Sheets

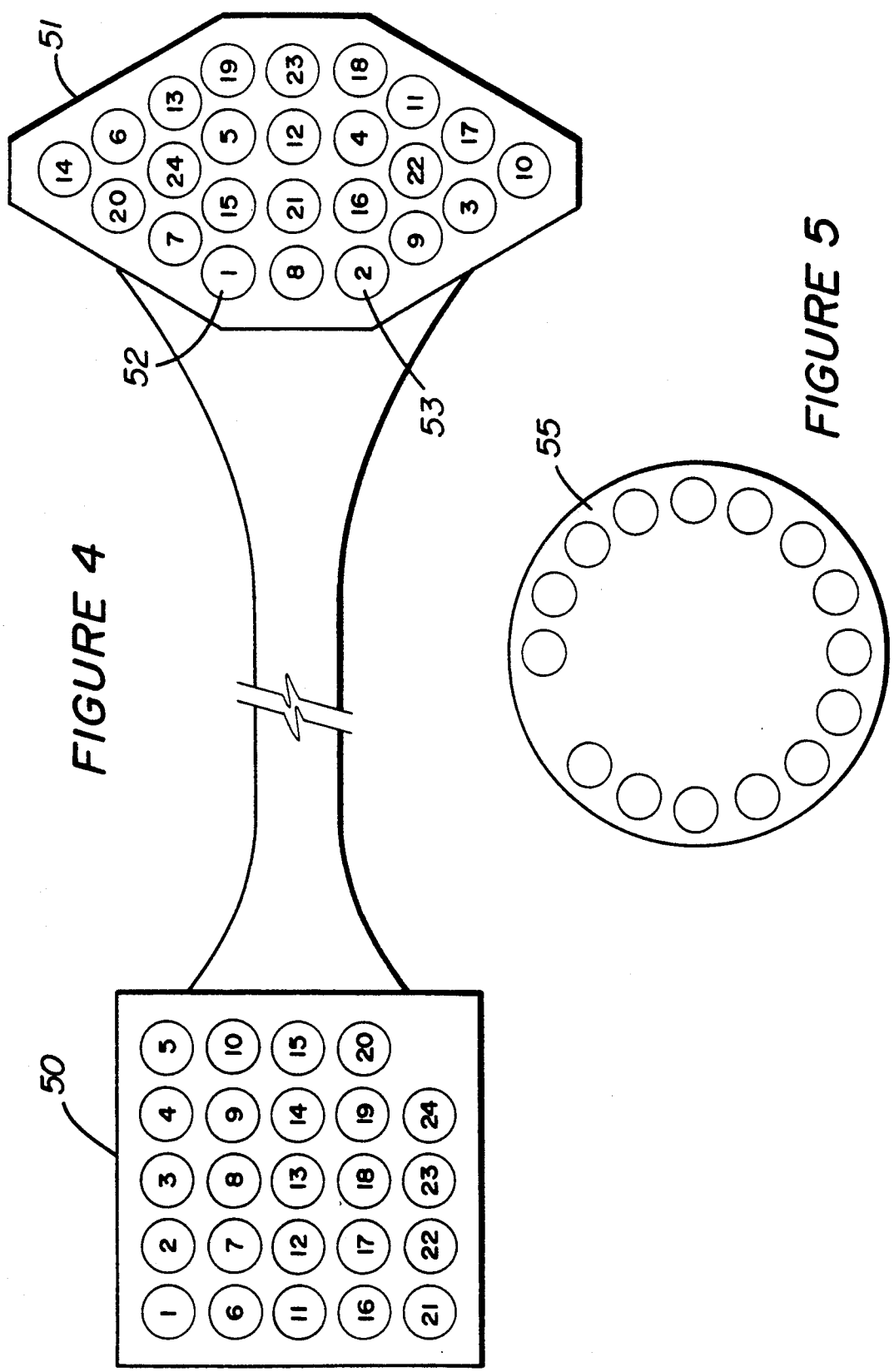

SYSTEM FOR CONTROLLED DISTRIBUTION OF LASER DOSAGE

FIELD OF THE INVENTION

The present invention relates to an instrument for distributing laser dosage in a treatment pattern, such as used in dermatology for the treatment of angiomas and the like.

DESCRIPTION OF RELATED ART

A condition known as the planar angioma occurs due to hypervascullation of the skin. This hypervascullation causes the skin to appear discolored. This discoloration is commonly known as a "port wine stain".

Current treatments for the planar angioma comprise closing off the blood vessels in the affected zone. This stops blood flow and the resultant discoloration in the hypervascullarized area.

The techniques used for closing off the blood vessels involve application of laser beams to the treatment zone. This effects closing off the blood vessels by photocoagulation, when the laser beam is generated at preferred wavelengths, as commonly known in the art.

The photocoagulation occurs due to thermal effects of the impact of the laser beam. In treating angiomas, the thermal effects desired occur in a specific temperature range. This elevated temperature range must be limited to the microvessels in the dermis in order to avoid any tissue damage and scar formation as a result of the procedure.

This laser treatment can be applied manually by a practitioner, or by means of an instrument such as disclosed in International Publication No. WO 87/06478 of International Patent Application No. PCT/FR87/00139, entitled SYSTEMATIZED TREATMENT INSTRUMENT, USING PARTICULARLY LASER ENERGY, USEFUL FOR EXAMPLE IN DERMATOLOGY.

The problems with the manual treatment are explained in the International Publication No. WO 87/06478, and include problems with regulating the distribution of the dosage of radiation and the like in a manner which avoids overexposing certain areas and underexposing other areas. Thus, the skill of the practitioner in applying the treatment is of utmost importance for the manually administered technique.

The International Publication No. WO 87/06478 provides a mechanized instrument for distributing the laser energy. This mechanized instrument involves delivering the laser beam in an optical fiber to a treatment head. In the treatment head, the end of the optical fiber is positioned using stepper motors to expose a set of elementary spots in a sequential scan pattern. A shutter in the treatment head is used to control the duration of pulses at each position in the scan pattern. While this technique has proved to provide great advances over the manual technique, it still suffers certain problems. In particular, the mechanism for positioning the fiber is quite complex and bulky. The shutter on the treatment head, which is used to control the duration of the pulses, is a source of failures because of the high repetition rates, and its position on the portable treatment head. Finally, the treatment head is heavy and uncomfortable to use.

Accordingly, it is desirable to provide an instrument for providing treatment of planar angiomas and the like, which is more durable, and easier to use for surgeons.

SUMMARY OF THE INVENTION

The present invention provides a mechanism for distributing the output beam from a laser system in a treatment pattern that overcomes many of the problems referred to above. In one aspect, the system comprises a plurality of optical fibers, having input ends and output ends. At the input ends, the fibers are secured in a scan configuration for receiving an output beam from a laser. At the output ends, the fibers are configured in a treatment configuration for distributing the output beam in a treatment pattern. A scanner coupled with the laser system directs the beam in a scan pattern at the input ends of the fibers which matches the scan configuration.

In one aspect, the scanner scans the beam through the scan configuration to supply pulses sequentially to the input ends of optical fibers in the scan configuration. The treatment configuration secures the output ends of the optical fibers so that the output end of one optical fiber sequentially receiving the beam from the scanner is non-adjacent the output end of a next optical fiber sequentially receiving the beam from the scanner.

It can be seen, therefore, that the scan configuration and treatment configuration can differ. This allows the ability to optimize the scan configuration on one end of the plurality of optical fibers to match the scanner mechanism used for directing the laser beam into the optical fibers. The treatment configuration can be independently designed without reference to the type of scanner utilized to provide an optimal pattern for a particular treatment.

Furthermore, because the treatment pattern is fixed, and all of the fibers for the treatment pattern are in position, the laser system can provide plural pulses of light simultaneously through the fiber bundle. This allows for more rapid treatment than is available in the system which relies on the successive positioning of a single fiber.

According to another aspect of the present invention, a system for delivering the laser beam is provided. The system includes a laser, a scanner, and a fiber bundle substantially as described above. The laser and the scanner are coupled with a data processor and other mechanisms for controlling the fluence of the laser beam in the treatment pattern.

The mechanisms that are operated in conjunction with the data processor include a shutter in the path of the laser beam, either near the scanner, or in the treatment head, for controlling the duration of pulses of the laser beam supplied in the treatment pattern. Also, the data processor can be utilized for adjusting the intensity of the laser beam delivered in the laser treatment pattern, in cooperation with an attenuator in the beam path, or by controlling laser output intensity directly.

Accordingly, the present invention allows for precise and reliable control of the treatment pattern, and the fluence of radiation applied in the treatment pattern. Furthermore, the treatment head can be manufactured in a compact format with no or few moving parts to increase reliability.

Other aspects and advantages of the present invention can be seen upon review of the figures, the detailed description, and the claims which follow.

BRIEF DESCRIPTION OF THE FIGURES

FIG. 4 is a schematic diagram illustrating the scan configuration and the treatment configuration for one embodiment of the present invention.

FIG. 5 illustrates yet an alternative embodiment of the scan configuration in the scanner head of the fiber bundle.

DETAILED DESCRIPTION

Figure 1:
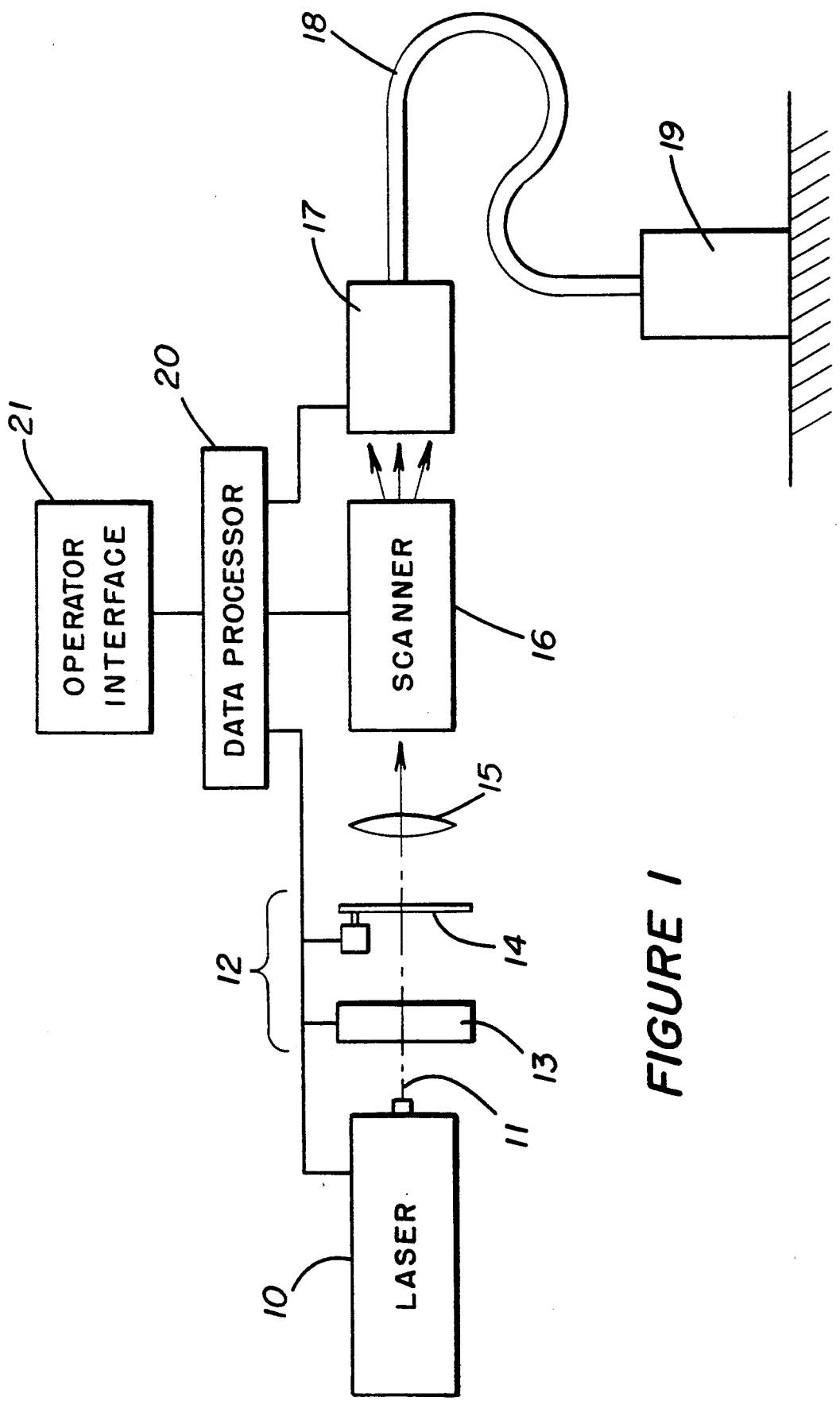
FIG. 1 is a schematic diagram of a laser system according to the present invention.

A detailed description of an embodiment of the present invention is provided with respect to the figures. FIG. 1 provides a schematic view of the laser system. FIGS. 2-5 illustrate the design of the fiber bundle.

The laser system includes a laser 10 generating a laser beam along path 11. In the preferred system, an Nd:YAG laser is used providing frequency-doubled output of 532 or 659 nanometers, such as is commercially available from Laserscope, Inc., San Jose, Calif. Also, other laser systems such as argon ion lasers, dye lasers, or copper vapor lasers commonly used in dermatology applications could be used. The invention can also be adapted for use with other intense light sources, like arc lamps or LEDs.

Beam path components 12 such as an attenuator 13 and a shutter 14 can be mounted with the system if desired. A lens 15 focuses the output of the laser along path 11 into a scanner mechanism 16. The scanner mechanism directs the laser beam into a scanner head 17 of a fiber bundle 18. The fiber bundle 18 is coupled from the scanner head 17 to a treatment head 19, which delivers the output pulses in a treatment pattern.

A data processor 20 is coupled with the laser 10, the beam path components 12, the scanner 16, and the fiber bundle 18 for providing control of the system. An operator interface 21 is coupled with the data processor for providing operator input and feedback.

Figure 2:
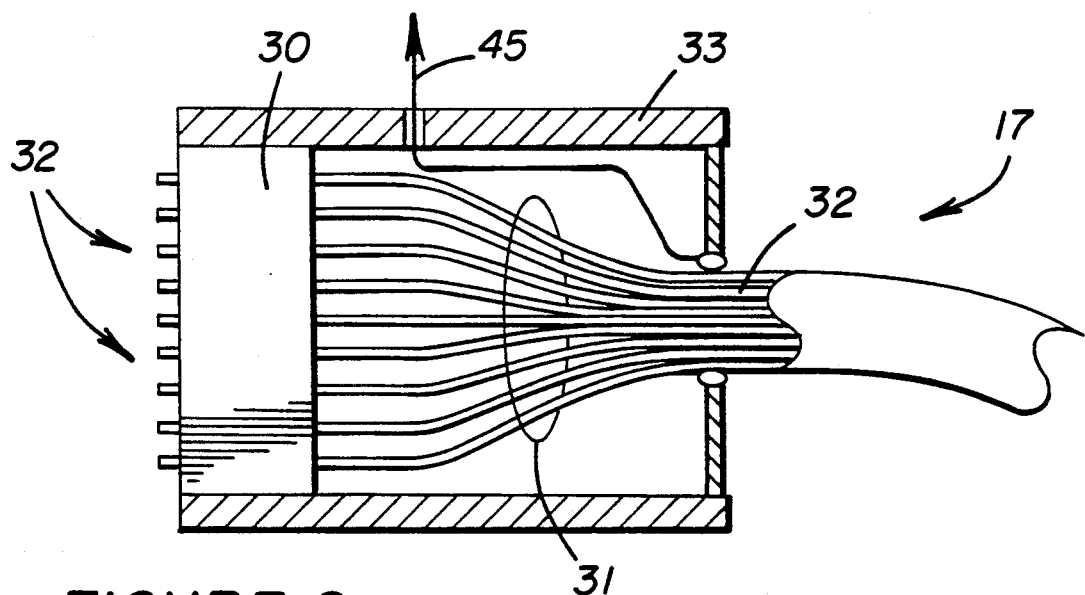
FIG. 2 illustrates schematically the scanner head of the fiber bundle.

The scanner head 17 is illustrated in FIG. 2. In the scanner head, a block 30 secures a plurality of optical fibers 31 in a scan configuration generally referred to by the reference numeral 32. The plurality of fibers 31 are coupled into a fiber bundle 32 which is connected at its opposite end to the treatment head. The block 30 may comprise a plastic, plexiglass or metal block having passages therethrough in a scan pattern. The optical fibers are individually placed in the passages in a scan configuration which matches the operation of the scanner 16. The block 30 and the fiber bundle 32 are secured in a frame 33 for suitable mounting adjacent the scanner 16. Connector 45 may be provided for communicating signals between the fiber bundles and the data processor 20.

Figure 3:
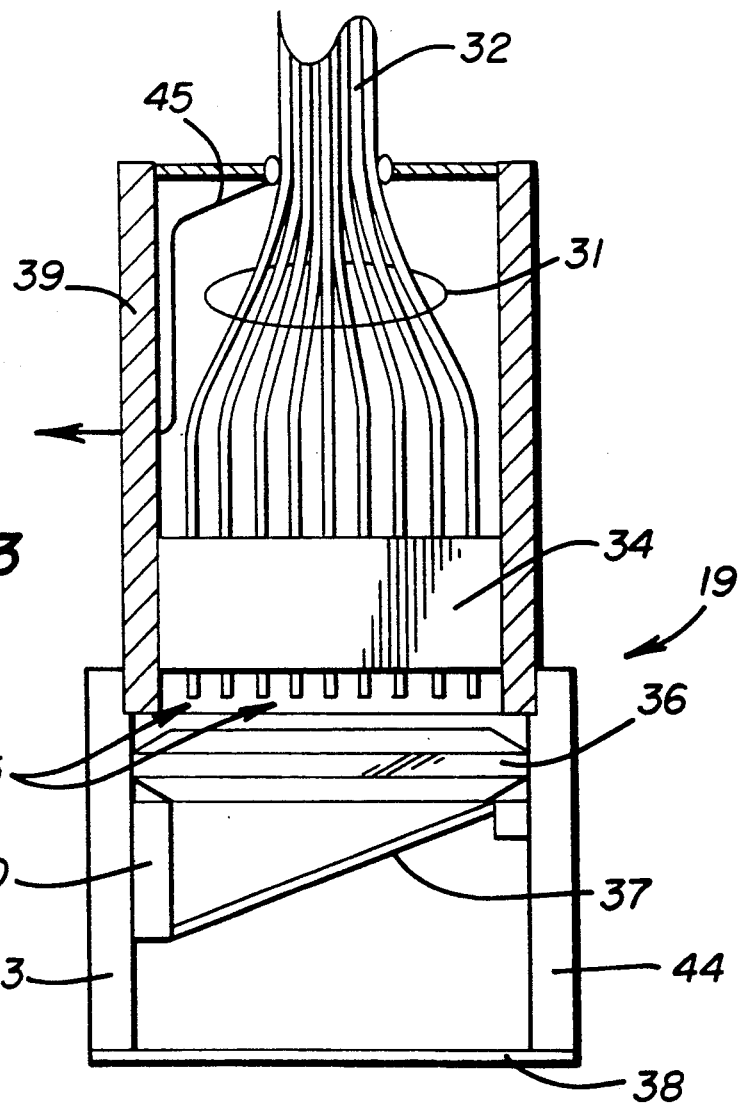
FIG. 3 illustrates schematically the treatment head of the fiber bundle.

One embodiment of the treatment head 19 is illustrated in FIG. 3. As can be seen, the fiber bundle 32 enters the treatment head, and the plurality of fibers 31 are distributed in a block 34 to provide a treatment pattern referred to generally by the reference numeral 35. A lens 36 and a beam splitter 37 are provided in the beam path from the output of the fibers 35. All of these elements are secured in a frame 39 which provides a durable tool that is easy to handle by a surgeon. A photodetector 40 is coupled with the beam splitter 37 and supplies a signal along connector 45 through the fiber bundle into the data processor 20 of FIG. 1 for use in controlling the intensity of the output beam. Coupled to the frame 39 is a template 38 mounted on stand-off posts 43, 44 for placement against a treatment zone on a body. The stand-off posts 43, 44 hold the fiber ends 35 a distance from the treatment zone on the body so that the lens 36 provides proper focusing of the pulses of laser light. Although not shown in FIG. 3, a safety shutter could be mounted in the treatment head if desired.

The block 34 is again a solid material having passages therethrough for receiving individual fibers in the scan pattern.

FIG. 4 schematically illustrates a scan pattern and a treatment pattern according to the present invention. Thus, in the scanner head, a scan pattern 50 such as shown in FIG. 4 could be established. In this scan pattern, an array of fibers in five rows and five columns, and numbered sequentially, is provided. First ends of the fibers in fiber bundle 56 are arranged in this scan configuration. The second ends of the fibers in the bundle 56 are then reorganized at the treatment head in a treatment pattern 51.

The treatment pattern 51 matches the preferred treatment sequence for a given application. The scan pattern 50 is designed to match the scanner technology utilized with the laser system. This scanner technology could be, for instance, a galvanometer controlled mirror which scans the output beam in a raster scan type pattern. This scanner could be operated in conjunction with the shutter 14 to provide controlled pulses of laser light in each of the fibers in a sequential fashion, under control of data processor 20.

The treatment pattern is adapted so that one fiber which sequentially receives a laser beam from the scanner is non-adjacent a next fiber which sequentially receives the laser beam from the scanner. Thus, the treatment end of fiber 1 at position 52 is not adjacent the treatment end of fiber 2 at position 53. Similarly, the treatment end of fiber 3 is not adjacent the treatment end of fiber 2. No two sequential fibers from the scan configuration 50 are adjacent one another in the treatment configuration 51.

It would be appreciated that in a commercial system, much larger number of fibers would be used. For instance, one commercial embodiment may include 127 fibers, each fiber from 0.4 to 0.6 millimeters in diameter, which are focused by the lens on the treatment head to illuminate spots 1-2 millimeters in diameter.

FIG. 5 illustrates an alternative embodiment of a scan configuration which could be utilized with a treatment configuration, similar to that shown in FIG. 4. In the configuration of FIG. 5, the inputs of the fibers are arranged in a circle 55. A scanner which could be beneficially utilized to scan a ring of fibers such as illustrated in FIG. 5 could comprise a mechanism including an optical fiber receiving the output of the laser, and having an output end coupled to a positioning mechanism, such as stepper motors which direct the beam individually into the respective fibers in the scan sequence 55.

In operation, the system of FIG. 1 receives instructions through operator interface 21 to provide a controlled systematized dosage of laser radiation to a treatment site. The fluence in joules per square centimeter is one such parameter provided by the operator interface. The data processor 20 operates controllable elements in the beam path to scan the beam into the appropriate fibers, and to control the fluence of the radiation in the treatment site.

The fluence can be controlled by controlling the duration of pulses, and/or the intensity of the beam being supplied into the fibers. The duration of pulses can be controlled by the shutter 14, or by operating a Q-switch within the laser cavity 10 or other techniques known in the art. Similarly, the intensity of the beam can be controlled using an attenuator 13 in the external beam path 12, or by controlling the pump energy supplied to the laser system 10 or other techniques well known in the art.

Where more rapid treatment is desired, the scanner 16 can be adapted to provide pulses of laser radiation to successive subsets of the optical fibers. For instance, optical fibers 1 and 2 could form a first subset. Optical fibers 3 and 4 a second subset, and so on. In this way, a greater area can be treated more rapidly. Referring to FIG. 4, it can be seen also that the treatment configuration can be arranged so that fibers in one successive subset are non-adjacent fibers in a next successive subset which receives the output of the laser.

The provision for placing sequential fibers or successive subsets of fibers non-adjacent to one another arises out of a need to control the build up of heat in the treatment zone, as explained in the above-referenced International Publication No. WO 87/06478. Heat from an illuminated spot is conducted outside the illuminated spot. If the next spot to be illuminated is in the zone heated by irradiation of a previous spot, then the amount of temperature rise of the tissue may indeterminate, or too high, causing damage to the tissue. Therefore, by spacing the sequential doses of laser radiation, the temperature rise is allowed to relax between the radiation of adjacent areas.

Accordingly, the present invention has provided a mechanism for distributing dosage of laser radiation which is particularly suited to dermatology, and the treatment of planar angiomas. It provides a treatment head which is durable, has few or no moving parts, and is lightweight. Furthermore, it allows precise control of the fluence of radiation applied using the technique.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An apparatus for distributing an output beam from an intense light source in a treatment pattern, comprising:
    a plurality of optical fibers, the fibers having input ends and output ends;
    first means, coupled with the input ends of the plurality of optical fibers, for securing the input ends in a scan configuration for receiving the output beam;
    means, coupled with the first means, for directing the output beam into the input ends of the plurality of optical fibers in the scan configuration;
    second means, coupled with the output ends of the plurality of optical fibers, for securing the output ends in a treatment configuration for distributing the output beam in a treatment pattern;
    wherein the treatment configuration secures the output ends of the plurality of optical fibers so that the output end of one optical fiber successively receiving the beam from the means for directing is non-adjacent the output end of a next optical fiber receiving the beam from the means for directing.

2. The apparatus of claim 1, wherein the means for directing includes:
    means, receiving the output beam, for scanning the beam to supply the beam sequentially to the input ends of optical fibers in the plurality of optical fibers in the scan configuration.

3. An apparatus for distributing an output beam from an intense light source in a treatment pattern, comprising:
    a plurality of optical fibers, the fibers having input ends and output ends;
    first means, coupled with the input ends of the plurality of optical fibers, for securing the input ends in a scan configuration for receiving the output beam;
    means, receiving the output beam, for scanning the beam to supply the beam into the input ends of successive subsets of the plurality of optical fibers in the scan configuration, wherein at least one of the successive subsets includes more than one optical fiber; and
    second means, coupled with the output ends of the plurality of optical fibers, for securing the output ends in a treatment configuration for distributing the output beam in a treatment pattern;
    wherein the output end of a member of the at least one subset including more than one optical fiber is non-adjacent to the output end of any other member of the at least one subset.

4. The apparatus of claim 3, wherein the treatment configuration secures the output ends of the plurality of optical fibers so that the output ends of one subset of optical fibers successively receiving the beam from the means for scanning, are non-adjacent the output ends of a next subset of optical fibers successively receiving the beam from the means for scanning.

5. The apparatus of claim 1, wherein the scan configuration is different from the treatment configuration.

6. A system for delivery of a laser beam for medical uses, comprising:
    a laser for generating a laser beam;
    a scanner, receiving the laser beam and directing the beam in a scan configuration;
    a plurality of optical fibers, the fibers having input ends and output ends;
    first means, coupled with the input ends of the plurality of optical fibers, for securing the input ends in the scan configuration for receiving the laser beam from the scanner;
    second means, coupled with the output end of the plurality of optical fibers, for securing the output ends in a treatment configuration for distributing the laser beam in a treatment pattern, wherein the treatment configuration secures the output ends of the plurality of optical fibers so that the output end of one optical fiber successively receiving the beam from the scanner is non-adjacent the output end of a next optical fiber receiving the beam from the scanner; and means, coupled with the scanner and the laser, for controlling fluence of the laser beam in the treatment pattern.

7. The system of claim 6 wherein the means for controlling comprises:
a shutter in the path of the laser beam, for controlling duration of pulses of the laser beam supplied in the treatment pattern.

8. The system of claim 6 wherein the means for controlling comprises:
means for adjusting intensity of the laser beam supplied in the treatment pattern.

9. The system of claim 6, wherein the means for controlling includes:
means for controlling the scanner to supply the beam sequentially to the input ends of optical fibers in the plurality of optical fibers in the scan configuration.

10. A system for delivery of a laser beam for medical uses, comprising:
a laser for generating a laser beam;
a scanner, receiving the laser beam and directing the beam in a scan configuration
a plurality of optical fibers, the fibers having input ends and output ends;
first means, coupled with the input ends of the plurality of optical fibers, for securing the input ends in the scan configuration for receiving the laser beam from the scanner;
second means, coupled with the output end of the plurality of optical fibers, for securing the output ends in a treatment configuration for distributing the laser beam in a treatment pattern;
means for controlling the scanner to supply the beam to the input ends of successive subsets of the plurality of optical fibers in the scan configuration, wherein the treatment configuration secures the output ends of the plurality of optical fibers so that the output ends of members of a given subset of optical fibers are non-adjacent to the output ends of other members of the given subset.

11. The system of claim 10, wherein the treatment configuration secures the output ends of the plurality of optical fibers so that the output ends of one subset of optical fibers successively receiving the beam from the scanner, are non-adjacent the output ends of a next subset of optical fibers successively receiving the beam from the scanner.

12. The system of claim 6, wherein the scan configuration is different from the treatment configuration.

13. A system for delivery of a laser beam for medical treatment in dermatology, comprising:
a laser for generating a laser beam;
a scanner, receiving the laser beam and directing the beam in a scan configuration;
a plurality of optical fibers, the fibers having input ends and output ends;
first means, coupled with the input ends of the plurality of optical fibers, for securing the input ends in the scan configuration for receiving the laser beam from the scanner;
second means, coupled with the output end of the plurality of optical fibers, for securing the output ends in a treatment configuration for distributing the laser beam in a treatment pattern, wherein the treatment configuration is different from the scan configuration;
means for controlling the scanner to supply the beam to the input ends of successive subsets of the plurality of optical fibers in the scan configuration, wherein the treatment configuration secures the output ends of the plurality of optical fibers so that the output ends of one subset of optical fibers successively receiving the beam from the scanner, are non-adjacent the output ends of a next subset of optical fibers successively receiving the beam from the scanner; and
means, cooperative with the means for controlling the scanner, for controlling duration of pulses of the laser beam supplied to the optical fibers in the successive subsets.

14. The system of claim 13, wherein at least one of the successive subsets of the plurality of optical fibers includes only one member.

* * * * *